(12) United States Patent
Reza

(10) Patent No.: US 6,780,444 B1
(45) Date of Patent: Aug. 24, 2004

(54) METHOD OF MAKING COSMETIC, PHARMACEUTICAL, AND DERMATOLOGICAL COMPOSITIONS AND COMPOSITIONS MADE ACCORDING TO THE METHOD

(76) Inventor: Alma Reza, 3 rue Cognacq Jay, 75007 Paris (FR)

( * ) Notice: Subject to any disclaimer, the term of this patent is extended or adjusted under 35 U.S.C. 154(b) by 343 days.

(21) Appl. No.: 09/171,670

(22) PCT Filed: Feb. 24, 1998

(86) PCT No.: PCT/FR98/00362

§ 371 (c)(1),
(2), (4) Date: Aug. 23, 1999

(87) PCT Pub. No.: WO98/37864

PCT Pub. Date: Sep. 3, 1998

(30) Foreign Application Priority Data

Feb. 25, 1997 (FR) ............................................. 97 02196

(51) Int. Cl.$^7$ ........................ A01N 65/00; A61K 35/78; A61K 6/00; A61K 7/00; A23N 1/00
(52) U.S. Cl. ........................ 424/765; 424/725; 424/735; 424/736; 424/758; 424/760; 424/777; 424/401; 99/495; 99/510; 426/599; 426/518; 426/416
(58) Field of Search ................................ 424/765, 725, 424/735, 736, 758, 760, 777, 401; 99/495, 510; 426/599, 518, 416

(56) References Cited

U.S. PATENT DOCUMENTS 4,971,813 A  * 11/1990 Strobel et al. .............. 426/387

FOREIGN PATENT DOCUMENTS

| FR | 2052080 | 4/1971 |
|----|---------|--------|
| FR | 2128265 | 10/1972 |
| FR | 2719473 | 11/1995 |

OTHER PUBLICATIONS

Grieve, M., A Modern Herbal, Papaw, at botanical.com, 1995.*

"Toiletries and cosmetics go bananas", *Soap, Perfumery Cosmetics*, vol. 58, No. 5, pp. 259–261, May 1985.

*Chemical Abstracts*, vol. 83: 130258 (1975). Fang–Yung et al., 'Calculation of blends of Preserved Fruit and Vegetable Juices'.

WPI/Derwent, AN 83–810823, Class A23L2/38; A61K 35/78, JP 58164515A (Shiraiwa T), abstract, Sep. 1983.

* cited by examiner

*Primary Examiner*—Sreeni Padmanabhan
*Assistant Examiner*—Lauren Q. Wells
(74) *Attorney, Agent, or Firm*—Leydig, Voit & Mayer, Ltd

(57) ABSTRACT

The invention concerns cosmetic and/or pharmaceutical and/or dermatological compositions and methods for preparing them. The composition is characterized in that it comprises a mixture called base mixture, consisting of a liquid extracted from a mixture (M) of tomatoes and apples once the spontaneous chemical reaction initiated by the mixture of the two crushed plants is completed. The invention is applicable to skin care.

24 Claims, No Drawings

METHOD OF MAKING COSMETIC, PHARMACEUTICAL, AND DERMATOLOGICAL COMPOSITIONS AND COMPOSITIONS MADE ACCORDING TO THE METHOD

This application is a 371 of PCT/FR98/00362, filed Feb. 24, 1998.

The present invention relates to in particular cosmetic and/or pharmaceutical and/or dermatological compositions intended in particular to promote the care of the skin. It also relates to the method of manufacture of such compositions.

At all times, one has sought to improve the aspect of the skin and in particular to delay or to eliminate the signs of its ageing. This ageing is reflected among others in the appearance of wrinkles and a loss of firmness of the skin due to a natural slowing down of the renewal of the living cells constituting this skin. The generally proposed solution is to eliminate the dead cells building up at the surface of the skin while promoting its cellular renewal.

The proposed cosmetic compositions are however most often based upon synthetic hence non-natural chemical products of which in addition the manufacture is complex and costly. The treatment of the skin however is not of aesthetic character only.

Thus acne and the lesions it causes originate from sebaceous glands associated with the pilose follicles in particular on the face, the back, the chest. These glands contain cells which secrete a mixture in particular containing triglycerides, fatty acids called "sebum". In acne, the sebum secretions are increasing, the ducts of the sebaceous glands are thickening and produce black points or comedos and inflammations appear about the sebaceous glands.

The main treatments known for acne either are not really effective (various gels and ointments) or exhibit serious inconveniences whether they are antibiotics (absorption of antibiotics for a long duration through oral or local route, the latter mode risking to create bacteria resistant to the antibiotics), or the retinoids (compounds closely related to the vitamin A which are administered in a hospital environment only and have incidences on the lever).

The eczema is as to it an inflammatory state of the skin characterized by groups of vesicular lesions of variable sizes. The known treatments are generally based upon steroids and/or antibiotics which are medicines which have sometimes serious inconveniences.

Psoriasis and parapsoriasis are pathological pictures which appear on any portion whatsoever of the surface of the body and which even may cover it entirely. The seriousness of the lesions depends on both the extension and the depth at which the psoriasic process affects the dermic layers. An important point of the pathology of psoriasis is that the regeneration of the epidermis is much quicker in the case of psoriasis than for a normal skin (3–4 days instead of 27 days).

Although the disease is known for a long time, the known therapeutics (ultraviolets, tars, dithranol—which should not be put in contact with the healthy skin—, steroids) are very little efficient and/or very penalizing for the patients.

In a both cosmetic and pharmaceutical field, the acids of fruits (alpha-hydroxy acids) which belong to a group of substances extracted from natural products such as citric acid (extracted from fruits), malic acid (extracted from the apple), lactic acid (extracted from milk) assume an increasing importance.

Thus they would be efficient in the treatment of various diseases of the skin, among which acne, in the fight against ageing due to the sun (heliodermy) and for the rejuvenation and the improvement of the aspect of the skin (removal of the wrinkles, increase of the freshness and of the tenacity of the skin).

Numerous pharmaceutical and cosmetic special products based upon acids of fruits are existing and new ones are appearing regularly.

However the use of these compounds and of compounds closely related to the vitamin A as chemical compositions exhibits the inconvenience of non-negligible or significant secondary effects.

The invention has as its object to cope with the foregoing inconveniences by proposing in particular cosmetic and/or pharmaceutical compositions based upon usual alimentary plants.

For that purpose, the invention proposes a composition characterized in that it comprises a mixture called basic mixture consisting of the liquid extracted from a mixture M of tomatoes and apples, once this spontaneous reaction initiated by the mixture of both plants in crushed form has finished.

According to another characteristic of this composition, the mixture M in addition comprises a gelling or thickening agent and/or an emollient agent.

Preferably this gelling or thickening agent will consist of peaches or persimmons and this emollient agent will consist of cucumbers.

When the mixture M does not comprise any gelling agent or emollient agent, it comprises apples and tomatoes with approximately equal weights.

When the mixture M comprises peaches or persimmons as a gelling or thickening agent or cucumbers as an emollient agent, it comprises between 30 and 35% of peaches or persimmons, between 30 and 35% of apples and about 30% of tomatoes as percentages by weight with respect to the weight of the final mixture (M).

Preferably it comprises between 25 and 30% of peaches or persimmons, between 20 and 25% of apples, between 20 and 25% of tomatoes and between 25 and 30% of cucumbers as percentages by weight with respect to the weight of the final mixture M.

According to another characteristic of the composition according to the invention, one adds a tenderizing or lysing agent to the said basic mixture.

This tenderizing or lysing agent will be more particularly selected in the group constituted by papaw, papain, chimopapain, trypsin, pineapple, latex of the fig tree or pepsin.

The preferred tenderizing or lysing agent of the invention is papaw. In this case one adds about one third by weight of papaw and about two thirds by weight of the said basic mixture.

The compositions according to the invention may in addition contain an acidifying agent. A preferred acidifying agent is lemon juice.

According to another characteristic of the composition according to the invention, one adds an irritating agent to the said basic mixture.

A preferred irritating agent is the cooking water of paprikas or green pimentos.

According to another characteristic of the composition according to the invention, one adds to the said basic mixture a mixture being both skin protecting since comprising substances acting against free radicals such as the vitamin C, the vitamin E, the beta-carotene, and skin-nutritive since comprising vitamins A, B, PP, amino-acids, carbohydrates, purins, fatty acids, calcium and oligo-elements such as iron, copper, manganese, sulphur, phosphorus, diode and possibly phospholipids.

In this alternative embodiment of the invention, the preferred nutritious or nutritive and protecting medium consists of cabbage juice or of the water of cooking, in preferably slightly mineralized water, of cabbages, preferably of green cabbages, possibly in admixture with juice from the cooking water of other plants.

More preferably, the nutritious medium consists of the water of cooking, preferably in slightly mineralized water, either of green cabbages or of a mixture in equal proportions by weight of green cabbages and of green salads with thick leaves such as lettuce.

In this case, one adds to one volume of the composition of the invention without any protecting and nutritive agent, three volumes of the said cooking water.

All these compositions of the invention may be used for the manufacture of a cosmetic and/or pharmaceutical composition intended to promote the care of the skin.

They may also be used for the manufacture of a cosmetic and/or pharmaceutical composition for the treatment of acne, of seborrhea, of psoriasis and of eczema.

In particular the invention proposes a bodily lotion for regenerating and making firmer the skin, which is characterized in that one adds to the said basic mixture or to the basic mixture admixed with a lysing or tenderizing agent, preferably papaw, the nutritious medium containing vitamins A, B, C, D, E, PP, amino-acids, calcium and oligo-elements such as iron, copper, manganese, sulfur, phosphorus, iode etc. and possibly an acidifying agent, preferably lemon juice.

A particularly preferred bodily lotion consists of one volume of the said basic mixture or of the said basic mixture admixed with papaw and of three volumes of the said cooking water and possibly of lemon juice.

Another subject of the invention is a cosmetic composition for the regeneration and the making firmer of the skin, the preventing of the wrinkles and the attenuation of the existing wrinkles, characterized in that it contains the said basic mixture or the said basic mixture admixed with a tenderizing or lysing agent, preferably with papaw and a thickener and/or a preservative and/or water and/or fats and/or hydrating fats and/or water/fats emulsifiers, cosmetically acceptable for an application as a cream or as a mask.

Another subject of the invention is a lotion improving the tolerance to the sun when applied before an exposure to the sun and alleviating the pain caused by an excessive exposure to the sun when applied after the exposure to the sun, characterized in that one adds to the so-called basic mixture or so-called basic mixture admixed with a tenderizing or lysing agent, preferably papaw, an agent containing compounds of the vitamin A such as vitamin A and the provitamin A, a nutritious medium containing vitamins A, B, C, D, E, PP, calcium and oligo-elements and optionally fat and/or water/fat emulsifiers.

In a preferred lotion of the invention improving the tolerance to the sun and alleviating the pain in case of excessive exposure to the sun, the agent containing compounds of the vitamin A consists of carrot juice.

A more preferred lotion is a lotion in which the said nutritive medium consists of the water of cooking, in preferably slightly mineralized water, of a mixture in equal proportions by weight of beetroots, green cabbages and spinaches and the said fat is raisin-seed oil.

A more particularly preferred lotion of the invention improving the tolerance to the sun and alleviating the pain in case of excessive exposure to the sun consists in equal proportions by volume of the said mixture denoted here as a basic mixture B admixed or not with a lysing agent or with an acidifying agent, of the said cooking water, to which mixture (B) one adds 20% by volume, with respect to the volume of the mixture (B), of carrot juice or of green cabbage juice and possibly of the fat and of the water-fat emulsifiers.

Still another subject of the invention is a shampoo for a normal scalp, characterized in that it consists of the said basic mixture or of the said basic mixture admixed with a lysing or tenderizing agent, preferably with papaw and possibly with an acidifying agent such as lemon juice and with a sufficient amount of shampoo to obtain a washing action. This shampoo may in addition be admixed with a nutritious medium containing vitamins A, B, C, D, E, PP, amino-acids, calcium and possibly phospholipids and oligo-elements.

In this case, a preferred nutritive medium consists of the water of cooking, in preferably slightly mineralized water, of one part by weight of green cabbages and of two parts by weight of spinaches and one adds three volumes of the said cooking water to one volume of the said shampoo.

Still another subject of the invention is a pharmaceutical and/or cosmetical composition called dermatological composition No. 2 for treating the slight states of psoriasis, acne and seborrhea, characterized in that one adds to the said basic mixture whether admixed or not with a tenderizing or lysing agent, preferably with papaw and with an acidifying agent, preferably lemon juice, an irritating agent and possibly a nutritious medium containing vitamins A, B, C, D, E, PP, amino-acids, calcium and possibly phospholipids and oligo-elements.

A preferred dermatological composition No. 2 of the invention is characterized in that the said irritating agent consists of green pimentos or red peppers and in that the said nutritious medium consists of the water of cooking, in preferably slightly mineralized water, either of green cabbages or of a mixture M of green cabbages and of green salads with thick leaves, preferably lattuce and of raw beetroots and in that one adds three parts by volume of the said cooking water to one volume of the said basic mixture whether admixed or not with a lysing agent or with an acidifying agent.

In this case, the said irritating agent consists of the cooking water of three green pimentos or red pimentos having a length of about 4 to 20 cm and the said nutritive agent or the said cooking water is obtained by cooking in one litre of preferably slightly mineralized water, either of green cabbages only or of about 80 g of green cabbages, 50 g of green salads with thick leaves and 100 g of beetroots.

The invention also proposes a pharmaceutical and/or cosmetic composition for the treatment in particular of acne, of seborrhea, of eczema and of psoriasis, characterized in that one provides a mixture (A) of the said basic mixture whether admixed or not with a lysing agent, preferably with papaw and with an acidifying agent, preferably lemon, with the dermatological composition No. 2 in combination with a pharmaceutically and/or cosmetically acceptable excipient such as a preservative or a geller and/or thickener for an application as a cream or as a lotion.

This composition is particularly characterized in that the mixture (A) consists of one third by volume of the said basic mixture whether admixed or not with a lysing or tenderizing agent, preferably with papaw, with an acidifying agent, preferably lemon juice and with two thirds by volume of the dermatological composition No.2.

A particular pharmaceutical composition for the treatment of psoriasis is a composition in which the mixture A consists of one third by volume of the basic mixture admixed with papaw and with two thirds by volume of the dermatological composition No. 2.

Another particular pharmaceutical composition for the treatment of eczema is a composition in which the mixture (A) consists of one sixth by volume of the basic mixture whether admixed or not with a lysing or tenderizing agent, preferably with papaw and an acidifying agent, preferably lemon juice and with five sixth by volume of the dermatological composition No. 2.

A pharmaceutical and/or cosmetic composition for the treatment of acne is a composition in which the mixture (A) consists of two thirds by volume of the said basic mixture whether admixed or not with a lysing or tenderizing agent, preferably with papaw and with an acidifying agent, preferably lemon juice, is one third by volume of the dermatological composition No. 2.

Another particular pharmaceutical and/or cosmetic composition for the treatment of seborrhea and/or of psoriasis of the scalp is a composition consisting of the mixture A in combination with a sufficient amount of shampoo to obtain a washing action. Preferably the said mixture A consists of one third by volume of the basic mixture admixed with papaw and of two thirds by volume of the dermatological composition No. 2.

The invention has also as its subject the method of manufacture of such in particular pharmaceutical and/or cosmetic and/or dermatological compositions, the method being of the type consisting in crushing and mixing together the starting ingredients, in letting them react chemically and then in filtrating the crushed mixture thus obtained to obtain on the one hand a solid and on the other hand a liquid, characterized in that the starting ingredients comprise apples, tomatoes and possibly a lysing agent and an emollient agent.

The use of a mixture of apples, tomatoes for the manufacture of a pharmaceutical and/or dermatological composition for the treatment of acne, of seborrhea, of psoriasis and of eczema falls also within the scope of the invention.

The invention will be better understood and further objects, characteristics, details and advantages thereof will appear more clearly in the course of the explanatory description which will follow.

The present invention is quite at first based upon the surprising discovery that:
a) the mixture by approximately equal weights of preferably green or yellow crushed apples and of also crushed raw tomatoes causes a spontaneous chemical reaction which lasts about 24 hours and which results in a heat evolution as well as in surprising properties for the mixture after the end of the chemical reaction;
b) the juice extracted from this mixture exhibits in an unexpected manner a stimulating and regenerating activity of the skin.

This activity appears in particular in the following form: a few minutes after the coating of the face of an individual with the juice extracted from a mixture in suitable proportions of tomatoes, apples, a strong feeling of heat is felt, a blotch appears and grows; after about twenty minutes, the blotch and the heat gradually decrease and then cease for leaving a feeling of freshness and of well-being. By then rinsing the face with water, the dead cells of the epidermis are eliminated. The intensity of the phenomenon and its duration depend on the type of skin and on the number of treatments undergone by the individual.

However since this juice is particularly active, one may add to the mixture of tomatoes, apples, a gelling and/or thickening agent and an emollient agent.

The preferred gelling agent here is peach or kaki, which fruits are both rich with pectin of which the gelling properties are known but of course any other gelling and/or thickening agent which will appear to the skilled man as suitable could also be used here, such as the gels usually known in cosmetics or hyaluronic acid also used in cosmetics.

The preferred emollient agent here is the cucumber, but of course any other emollient agent which will appear to the man skilled in the art as being suitable could also be used here.

One assumes that the activity of the juice extracted from this mixture of apples and tomatoes, admixed with the emollient agent, which juice one will call here basic mixture in the following, is due among others to the spontaneous chemical reaction and to the presence of acids of fruits, of vitamin A, vitamin PP, vitamin E.

To facilitate the application and still further improve the comfort of the individual this mixture may be integrated into a cosmetically or pharmaceutically acceptable excipient.

This basic mixture may be completed with other plants or substances for having either less strong effects than those of the basic mixture and permitting in particular to provide bracing lotions and shampoos or on the contrary stronger effects in particular for being able to provide the effect previously described in depth, i.e. in the derm and no longer at the surface of the skin only.

This action in depth may be obtained through addition to the basic mixture of crushed papaws. Here again one assumes that the papaw performs the function of an agent tenderizing the epidermis or the derm. One may also use vegetable products known for their digestive and tenderizing properties for meat, such as the pine-apple, the latex of the fig tree as a substitution for the papaw or chemically pure or refined products contained in the papaw, the pineapple, the latex of the fig tree such as papain, chimopapain, bromelin, pepsin or trypsin.

The ratios of the weights of all the vegetables entering the different compositions described here are not critical for observing the effect but for having a maximum intensity of this effect and for not depending on compositions of each plant which vary in an appreciable manner from one batch to the other one as every natural product, the following proportions in percentages by weight with respect to the weight of the final mixture to be obtained are particularly preferred:
a) in the case of a basic mixture which does not integrate any gelling and/or thickening agent or emollient agent, one should take equivalent rates of apples and of tomatoes;
b) in the case of a basic mixture integrating a peach-based or kaki-based gelling agent, one should take between 35 and 40% of peaches or kakis, between 30 and 35% of apples and about 30% of tomatoes in percentages by weight with respect to the weight of the final mixture to be obtained;
c) in the case where one wants to obtain a lenitive and emollient action in particular with cucumber, one should take between 25 and 30% of peaches or kakis, between 20 and 25% of apples, between 20 and 25% of tomatoes and between 20 and 25% of cucumbers.

The mixture obtained from these vegetables is provided in a simple manner at ambient temperature and by using food treatment techniques fruits and vegetables are cut to pieces with the skin.

The mixture thus obtained is then chopped up and then blended in an alimentary mixer. This mixture is then filtrated on a filter the mesh diameter of which is 0.5 mm or less for extracting the liquid.

Although the most active part be the liquid, one may not filtrate the crushed mixture and use it as such as the basic mixture as defined here.

To obtain the stability in the time, a cosmetically and/or pharmaceutically acceptable preservative should be added.

The liquid or basic mixture thus obtained becomes really active after 24 h only after the end of the preparation.

This basic mixture may be used by way of an application every five days at a maximum with an effect of desquamation, making firmer and regeneration of the skin, preventing off the wrinkles and attenuation of the existing wrinkles and it may serve for preparing other compositions.

Thus one will be able to add to this basic mixture an acidifying agent. A preferred acidifying agent is lemon juice in view of its known actions on the skin: action of discoloration of the skin, cleaning of the fatty skins, making the skin and the nails firmer. But any other acidifying agent known to the man skilled in the art will also be suitable.

One will also be able to add a nutritious medium containing vitamins A, B, C, D, E, PP, calcium, amino-acids, possibly phospholipids and oligo-elements such as iron, copper, manganese, sulphur, phosphorus etc.

A preferred nutritious medium consists of the water of the cooking of some vegetables.

To obtain this cooking water, the use of weakly mineralized water is sufficient for carrying out the cooking. It is not useful to use distilled water, thereby further simplifying the carrying out of the invention. And this is an additional advantage of the invention.

One will now describe by way of examples only given as being indicative only and not limiting, applications of the said basic mixture either or not admixed with an acidifing agent and a tenderizing or lysing agent and/or an irritant agent.

One should recall that in these examples too, the proportions by weight or by volume are not critical but proportions close to those stated are however recommended.

With closely related proportions, one understands a variation of about plus or minus 30% with respect to what is specified.

EXAMPLE 1

Body lotion for making the skin firmer and eliminating the dead cells.

To obtain this body lotion, one blends one volume of the basic mixture either admixed or not with lemon juice, with three volumes of the water of the cooking of a mixture of green cabbages and of green salads with thick leaves, preferably lattuces.

Advantageously to obtain the cooking water in question, one will cause 100 g of green cabbages and 100 g of green salads with thick leaves to boil in one litre of weakly mineralized water for 20 mn.

One may add to this body lotion a cosmetically acceptable preservative and/or gelling and/or thickening agent as well as fats and water/fats emulsifiers.

If one desires an action more in depth, one may also add crushed papaw or other lysing agents.

EXAMPLE 2 cosmetic composition for the regeneration of the skin and making it firmer, the preventing of wrinkles and the attenuation of the existing wrinkles.

The basic mixture either admixed or not with papaw and/or lemon juice is a mixture with a cosmetically acceptable thickener and/or preservative and/or water and/or fats and/or hydrating fats for an application as a cream or as a mask.

One may in particular use as an excipient, cosmetic creams of the type of those sold on the market.

EXAMPLE 3

Lotion permitting to increase the tolerance to the sun when it is applied before exposure to the sun and to alleviate and to relieve the pain pursuant to an excessive exposure to the sun.

One volume of the said basic mixture either or not admixed with papaw and/or lemon juice is blended with one volume of the water of the cooking, in weakly mineralized water, of a mixture in equal proportions by weight of beetroots, green cabbages and spinaches.

One should add to the mixture called mixture B thus obtained one volume of carrot juice equal to 20% of the volume of this mixture B.

Advantageously, the cooking water is obtained by causing 100 g of raw beetroots, 100 g of green cabbages and 100 g of spinaches to boil for 20 mn in one litre of weakly mineralized water.

One may possibly add fat and water/fat emulsifying agents, hydrating agents or even a hydrating cream of the type of those sold on the market to obtain at the same time a complementary effect of hydratation.

One may as previously add to this lotion preservatives and thickeners to facilitate and improve the application of this lotion.

The carrot juice gives the skin a coloration but this is not its sole effect. It acts in synergy with the basic mixture and as an agent containing compounds of the vitamin A such as the vitamin A and the provitamin A. Thus any other agent supplying these compounds could be used here.

In particular, the previous lotion exhibits the inconvenience of risking to stain the garments. An alternative composition which does not exhibit this inconvenience consists in replacing the carrot juice with green cabbage juice which is almost as rich in beta-carotene as carrot juice.

EXAMPLE 4

Shampoo for Normal Scalp.

To one volume of the basic mixture either or not admixed with papaw and/or lemon juice, one adds three volumes of water of the cooking of one part by weight of green cabbages and of two parts by weight of spinaches. One then introduces a sufficient amount of shampoo to obtain a washing action.

Preferably the cooking water is obtained by causing 100 g of green cabbages and 200 g of spinaches to boil for 20 mn in one litre of weakly mineralized water. One blends three volumes of this cooking water with one volume of the basic mixture. One possibly adds 100 to 140 drops of lemon juice to about one litre of the previous mixture.

One adds shampoo sufficiently for having a washing action. One understands here with a normal scalp a scalp exhibiting no excess of seborrhea or dermatological diseases.

EXAMPLE 5

Cosmetic and/or pharmaceutical composition called dermatological composition No. 1 for attenuating and/or eliminating the slight states of seborrhea and acne.

One blends in a mixer two thirds by weight of the basic mixture either or not admixed with lemon juice, with one third by weight of papaw.

The papaw is cut up with the skin and the flesh while not taking the seeds.

EXAMPLE 6

Cosmetic and/or pharmaceutical composition called dermatological composition No. 2 for attenuating and/or eliminating the slight states of psoriasis, of acne and of seborrhea.

One mixes three volumes of the water of the cooking of three cut green or red pimentos with a length comprised between about 4 cm and about 20 cm and of a mixture of green cabbages, green salads with thick leaves, preferably lattuce, raw beetroots and of green or red pimentos with one volume of the dermatological composition No. 1.

Preferably one will obtain the aforesaid cooking water by causing three cut up green or red pimentos with a length comprised between about 4 cm and about 20 cm and 80 g of green cabbages, 50 g of green salads with thick leaves, 100 g of raw beetroots to boil for 25 mn in one litre of weakly mineralized water.

The pimentos here perform the function of an irritant agent. As such, any irritant agent, which would appear to the man skilled in the art, could be used. In particular, any substance providing capsaicin or a member of the family of the capsaicinoids could be used.

One thus obtains a composition which, in an unexpected manner, has a selective desquamation effect limited to the horny skin or to the skin affected by diseases such as psoriasis, acne and seborrhea.

The successive applications of the dermatological composition No. 2 onto the non healthy skin result in a gradual desquamation, the effect of each application being limited to an external layer of the skin. The application of the dermatological composition No. 2 onto the sound skin on the contrary has a slightly irritating effect which however results in no desquamation.

The repeated applications of the dermatological composition No. 2 onto the sound skin exhibit no inconveniences as long as they are not extended and systematical.

By making mixtures of the dermatological compositions No. 1 and No. 2, one obtains compositions which in an unexpected manner permit to treat disorders or diseases of the skin such as acne, seborrhea, eczema and psoriasis.

The mixtures of the dermatological compositions No. 1 and No. 2 may either be made in advance in a fixed manner or on the contrary in an advantageous manner developed in the course of time to promote at first one type of effect and then the other one or originate from alternate applications of both compositions.

EXAMPLE 7

Pharmaceutical composition for the treatment of psoriasis.

A particularly preferred composition for the treatment of psoriasis consists of a mixture of one third by volume of the dermatological composition No. 1 and of two thirds by volume of the dermatological composition No. 2.

Preferably this mixture is applied for three days per week twice one and a half hour onto the affected parts. Here also to facilitate the application and improve the comfort of the patient, this composition could be admixed with a thickener and/or a preservative.

EXAMPLE 8

Pharmaceutical composition for the treatment of eczema.

A preferred composition for treating eczema consists of a mixture of one sixth by volume of the dermatological composition No. 1 with five sixth by volume of the dermatological composition No. 2.

Preferably this composition is applied for three days per week twice one and a half hour onto the affected parts.

Once more, this composition could be mixed with an excipient such as a thickener, a preservative etc. to improve the comfort of the patient and to facilitate the application as a cream or as a mask.

EXAMPLE 9

Composition for the treatment of acne.

A preferred mixture permitting to treat acne consists of two thirds by volume of the dermatological composition No. 1 and of one third by volume of the dermatological composition No. 2 either or not admixed with already cited excipients.

Preferably this composition is applied for three days per week twice one and a half hour onto the affected parts.

EXAMPLE 10

Pharmaceutical and/or cosmetic composition for the treatment of seborrhea and/or psoriasis of the scalp.

This composition consists of a mixture of one third by volume of the dermatological composition No. 1 and of two thirds by volume of the dermatological composition No. 2 to which one adds shampoo sufficiently for obtaining a washing action.

This composition is particularly interesting since it permits to obtain a treatment of the scalp easy and simple to be used since it consists in merely washing the hair on an average three times a week.

The cosmetic and/or pharmaceutical in particular dermatological compositions according to the present invention may be prepared in forms suiting various modes of administration. In particular they may present themselves in a form intended for the superficial administration onto the skin or the scalp such as a cream, a milk, a gel or a lotion in order to stimulate and to regenerate or to treat the skin.

A non negligible advantage of the invention is to provide pharmaceutical and/or cosmetic compositions which are preserved for a sufficiently long duration (about 18 months at ambient temperature and light). This limits most of the storage and stocking problems without having to provide the isolation of any active substance, these methods of isolation in general being long and expensive.

The invention is of course not at all limited to the embodiments described and illustrated which have been given by way of examples only.

Thus for example it will allow to obtain a composition permitting to remove the blotches, onsets of eczema and other skin problems of the infants without causing traumatizing and dangerous chemical compounds to intervene on such subjects.

It will likewise allow to remove the blisters occurring pursuant to small burns such as the usual domestic burns if the mixture is applied onto the burned skin very quickly after the burn.

It will also permit to accelerate the healing of the wounds resulting from cuts or from localized frictions by applying the mixture.

Likewise although in the examples, one has expressly made reference to the papaw, it is well understood that any other tenderizing or lysing agent could be used in an equivalent manner.

In the same fashion, although one has described compositions containing the water of the cooking of some particular vegetables, it should be well understood that any other nutritious medium containing vitamins A, B, C, D, E, PP, calcium, amino-acids and possibly phospholipids and oligo-elements could be used in an equivalent manner.

Even more, some compositions of the invention could be used as alimentary compositions to obtain a systemic effect.

On the contrary, the invention comprises all the equivalents of the means described as well as their combinations if the latter are carried out according to its gist.

What is claimed is:

1. A method for manufacturing a composition comprising crushing tomatoes and apples, mixing the crushed tomatoes and apples together in a weight ratio of tomatoes to apples between 0.8 and 1.25 to produce a mixture (M), allowing the mixture (M) to stand for about twenty-four hours, and filtering the mixture (M) after the standing for about twenty-four hours to produce a filtered liquid as the composition.

2. The method according to claim 1, including diluting the mixture (M) and adding an emollient.

3. The method according to claim 2, wherein the emollient is cucumber.

4. The method according to claim 3, including blending a gelling agent with the mixture (M).

5. The method according to claim 4, wherein the gelling agent is one of peach and persimmon.

6. The method according to claim 4, wherein the gelling agent is a cosmetically and pharmaceutically acceptable agent.

7. The method according to claim 5, wherein the composition includes between 35 and 40% of one of peaches and persimmons, between 30 and 35% of apples, and about 30% of tomatoes, by weight.

8. The method according to claim 5, wherein the composition consists of between 25% and 30% of one of peaches and persimmons, between 20 and 25% of apples, between 20 and 25% of tomatoes, and between 25 and 30% of cucumbers by weight.

9. The method according to claim 1 including adding one of a tenderizing and lysing agent to the mixture (M).

10. The method according to claim 9, including adding a lysing agent wherein the lysing agent is selected from the group consisting of papaw, papain, chimopapain, trypsin, pineapple, latex of the fig tree, and pepsin.

11. The method according to claim 9, including adding a tenderizing agent wherein the tenderizing agent is papaw.

12. The method according to claim 11, including mixing about one third by weight of papaw with about two thirds by weight of the mixture (M).

13. The method according to claim 1, including adding an acidifying agent to the mixture (M).

14. The method according to claim 13, wherein the acidifying agent is lemon juice.

15. The method according to claim 1, including adding an irritant agent.

16. The method according to claim 15, wherein the irritant agent is capsaicin.

17. The method according to claim 15, wherein the irritant agent is water in which pimentos have been cooked.

18. The method according to claim 1, including adding a nutritious and protective medium containing vitamins A. B, C, D, E, PP, calcium, beta-carotene, amino-acids, carbohydrates, sterols, purins, fatty acids, and, optionally, phospholipids and oligo-elements such as iron, copper, manganese, sulphur, phosphorus, and iodine to the mixture (M).

19. The method according to claim 18, wherein the nutritive and protective medium includes one of cabbage juice and water in which cabbages have been cooked.

20. The method according to claim 18, wherein the nutritive, and protective medium consists of water in which green cabbages and green salad with thick leaves, such as lettuce, have been cooked.

21. The method according to claim 19, including mixing together one volume of the composition obtained according to claim 17, and three volumes of the water.

22. A body lotion comprising the composition obtained by the method according to claim 18.

23. A shampoo comprising the composition obtained by the method according to claim 1.

24. A shampoo comprising the composition obtained by the method according to claim 18.

* * * * *